United States Patent [19]
Löbering et al.

[11] Patent Number: 5,397,567
[45] Date of Patent: Mar. 14, 1995

[54] GEL, ESPECIALLY FOR OPHTHALMOLOGY

[75] Inventors: Hans-Georg Löbering, München; Heinz Polzer, Taufkirchen, both of Germany

[73] Assignee: Medproject Pharma Entwicklungs Und Vertriebs Gesellschaft mbH, Sauerlack, Germany

[21] Appl. No.: 37,991

[22] Filed: Mar. 25, 1993

[30] Foreign Application Priority Data

Mar. 25, 1992 [DE] Germany .................... 42 09 722.3

[51] Int. Cl.⁶ .................... A61K 31/74; A61F 2/14
[52] U.S. Cl. .................... 424/78.04; 424/427; 424/428; 514/772.2; 514/777; 514/912; 514/913; 514/914; 514/915
[58] Field of Search ............... 424/427, 428, 487, 488, 424/78.04; 514/912, 913, 914, 915, 772.2, 777

[56] References Cited

U.S. PATENT DOCUMENTS

| | | | |
|---|---|---|---|
| 4,524,064 | 6/1985 | Nambu | 424/81 |
| 4,983,385 | 1/1991 | Hasegawa | 424/78 |
| 5,013,769 | 5/1991 | Murray et al. | 523/111 |
| 5,188,826 | 2/1993 | Chandrasekaran et al. | 424/78.04 |

FOREIGN PATENT DOCUMENTS

0312208A1 4/1989 European Pat. Off. .
0280737A1 9/2988 European Pat. Off. .

*Primary Examiner*—Thurman K. Page
*Assistant Examiner*—Carlos Azpuru
*Attorney, Agent, or Firm*—Woodcock Washburn Kurtz Mackiewicz & Norris

[57] ABSTRACT

An ophthalmologic gel is disclosed having a viscosity in the range of about 10,000 to about 50,000 mPa.s and comprising (1) about 0.05 to about 3% by weight of one or more polyacrylates and (2) about 0.1 to about 10% by weight one or more water-soluble, physiologically compatible polymers selected from the group consisting of polyvinyl alcohol, dextran, and mixtures thereof.

23 Claims, No Drawings

GEL, ESPECIALLY FOR OPHTHALMOLOGY

BACKGROUND OF THE INVENTION

This invention pertains to new medications, namely gels, especially for use on the eye.

Generally, active ingredients for use in the eye are supplied in the form of salves, drops, inserts, or even gels. Each of these forms of administration has its advantages and disadvantages. The form of treatment most pleasant for the eye is still the aqueous drop. In contrast to the other forms mentioned, however, it has the shortest residence time on the eye, which means that the treatment frequency is correspondingly higher and the systemic stress thus greater.

The development of gels which reside for a longer period of time on the surface of the eye has therefore been attracting greater attention. These gels frequently have a salve-like consistency and are therefore packaged in tubes. The handling of tubes for the administration of a drop to the eye has disadvantages in many respects, for which reason physicians and patients prefer eye medications in plastic bottles. So far there is no product which logically combines the advantages of aqueous drops, namely, their compatibility and ease of handling, with the advantage of a prolonged residence time on the eye. Although several patents on gels and gel formulations have appeared, the special requirements associated with the use of a gel on the eye have not yet been worked out in them.

Gels based on the use of carbomer (polymer based on acrylic acid) and mixtures of carbomer with other polymers are known. Especially in connection with uses in the eye, carbomer gels have the property of undergoing a considerable change in consistency after administration. A desirable, water-supplying effect is associated with this property, as a result of which this gel offers advantages, especially in the case of dry eyes. To achieve at the same time a residence time on the eye which is longer than that of pure aqueous drops, however, the concentration of the carbomer must be so high that the gel has a relatively high viscosity and thus can be dispensed only from tubes, which is therefore disadvantageous with respect to administration.

Mixtures of carbomer with other polymers for the production of gels have been developed primarily for dermatological purposes in the form of "adhesive salves" and in the form of "gel plasters" for covering wounds (e.g., U.S. Pat. No. 4,524,064; U.S. Pat. No. 5,013,769; European Patent No. 280,737 Al). Although in these cases a gel must be prepared in a preliminary stage, the goals pursued by the product are quite different, namely, to cover wounds. For this purpose, the product must be nearly insoluble in water and elastic; it is also required to undergo very little shrinkage and to adhere firmly to the skin. In this type of application, the absorption of wound secretions is especially important. The gels in question acquire this property by the incorporation of a large amount of a water-binding agent such as sorbitol, mannitol, etc. A concentration of sorbitol, etc., which is significantly higher than the isotonic concentration is harmful to the eye. Necessarily, therefore, the properties which derive from the formulations claimed in the patents cited above are quite different and in fact tend to be unfavorable for use in the eye, inasmuch as these preparations remove moisture and show poor compatibility because of the high concentrations they contain. Eye inserts are known to exert similar effects.

Another patent (U.S. Pat. No. 4,983,385) pertains to an improvement to the adhesion behavior of fat-containing salves especially with respect to moist body surfaces such as mucous membranes. This problem is solved by the incorporation of carbomer and other water-soluble polymer mixtures into the aqueous phase of the salve.

Another patent (European Patent No. 312,208 Al) describes aqueous gels, but each of these contains only a single polymer. Here, too, none of the special requirements associated with use in the eye (e.g., with respect to compatibility and form of administration) is taken into account.

The known gels do not offer all of the advantages sought for an ophthalmologic gel. It is an object of this invention to provide such gels that can be applied in the form of gels and be dispensed from standard commercial eye drop bottles. The original viscosity of the gel is the key factor which determines drippability. Drippability ensures greater ease of handling, because the product can be dispensed from a standard commercial eye drop bottle. The accuracy with which the contents can be measured is much better from bottles than from tubes, from which a gel usually emerges in the form of a "strand". Suitable original viscosities are in the range of about 10,000–50,000 mPa.s (the viscosity values are based on the measurement with a Brookfield viscometer, as described in the examples).

It is further an object of this invention to provide gels having an adjustable residual viscosity on the eye. A certain residual viscosity develops on the eye as a result of the mixing of the gel with components of the lachrymal film, primarily the inorganic salts. Because of the known properties of carbomers (collapse of the gel structure), this residual viscosity is much lower than the original viscosity as it exists before contact with the lachrymal fluid. The residual viscosity which develops on the eye is the factor which ultimately determines the compatibility and the residence time of the gel on the surface of the eye. Both the duration of the activity and the intensity of the activity of the eye medication are increased by an increase in the residual viscosity. A residual viscosity which is too high, however, leads to adhesive effects, to the feeling of the presence of a foreign body, and thus to compatibility problems. Suitable residual viscosities are in the range of 20–2,000 mPa.s.

It is further an object of this invention to provide gels into which active ingredients and preservatives normally used in ophthalmology may be incorporated. Because precipitations can occur occasionally through interactions between the carboxyl groups of the carbomer and organic bases in particular, there are limits on the amounts of active ingredients and preservatives which can be incorporated into carbomer gels. Most of the active ingredients used in ophthalmology consist of organic bases or their salts. Several important preservatives also belong to this class of compounds.

In arriving at a gel which meets these objectives, the problem was to manage two effects which proceed in opposite directions, namely, the original and the residual viscosities. For a gel to be capable of administration in the form of drops, it is necessary for its original viscosity to be relatively low, which means that it can contain only a relatively small amount gel-forming material. As a rule, this usually means that the residual viscosity after administration to the eye will be rather low. It will be so low, in fact, that hardly any noticeable improvement will be achieved in the residence time of the gel on the eye. If the amount of gel-forming material used (carbomer) is increased to achieve a more suitable (higher) residual viscosity, the result is an original viscosity which in practice no longer allows the product to be dispensed in the form of drops from a bottle. Through the effective addition of salts (inorganic salts, including the salts of organic amines and amino acids) to these gels with a high original viscosity, however, the original viscosity can be reduced to a point at which satisfactory drippability can be achieved.

It was desired to develop a gel formulation which exhibits a defined ratio of original to residual viscosity, the goal being to produce a drippable gel with a prolonged residence time on the surface of the eye. However, since the incorporation of active ingredients and possibly of preservatives must also be taken into account, it turned out to be impossible to accomplish this task simply by discovering a suitable carbomer concentration and then by adding a salt, i.e., by exploiting the known properties of carbomers. On the contrary, it was necessary to discover a new formulation which would be suitable.

SUMMARY OF THE INVENTION

Novel gels meeting the objects outlined above have been found. These gels, suitable for ophthalmologic use, have a viscosity in the range of about 10,000 to about 50,000 mPa.s and comprise (1) about 0.05 to about 3% by weight of one or more polyacrylates and (2) about 0.1 to about 10% by weight of one or more water-soluble, physiologically compatible polymers selected from the group consisting of polyvinyl alcohol (PVA), dextran, and mixtures thereof. These gels have been found to be suitable with respect to ability to be formulated and good compatibility in the eye.

DETAILED DESCRIPTION OF THE INVENTION

Gels of this invention comprising carbomer and PVA are preferred. It has been found that PVA not only acts as a solubilizer but also offers additional film-forming properties. This is an effect which is especially desirable in connection with use in the eye. The mixture of carbomer and PVA thus offers advantages over pure carbomer gels even in a form which is free of active ingredients.

The surprising discovery was made that it is difficult to produce stable gels from carbomer and PVA. Because gels for use on the eye must be sterile, it is absolutely necessary for the finished product to be autoclavable. Very high requirements must therefore be imposed on the temperature stability of these gels. This also applies, of course, to the required shelf-life of the finished product in its final container over the course of the product's lifetime. The stress condition resulting from exposure to heat simultaneously provides information on the shelf-life and long term stability. According to the invention, it was discovered that not every mixing ratio of carbomer to PVA leads to products which are stable in terms of their general features, especially their original viscosity (see Table I).

According to the invention, any standard commercial grades of carbomer (grades of polyacrylate) can be used. It is advisable to select water-soluble grades with a molecular weight in the range of 1,000,000–4,000,000; in concrete terms, such carbomers include the Carbopols 934, 934P, 940, 941, 951, 954, 974, 974P, 980, and 981 (B. F. Goodrich, Cleveland, Ohio). (See also H. P. Fiedler: Lexikon der Hilfsscoffe filr Pharamezie, Kozmecjk und angrenzende Gebiece (Dictionary of Auxiliary Substances for Pharmacy, Cosmetics, and Related Areas), 3rd edition, Edition Cantor Aulendorf, 1989; key words: polyacrylic acid, carbopol). The PVA is preferably an incompletely saponified grade (i.e., degree of hydrolysis, at least 99%; molecular weight, 15,000–200,000).

To provide gels with a stable viscosity and a stable pH, the amount of (1) polyacrylate is preferably equal to or less than the amount of (2) PVA and/or dextran. More preferably, the ratio of component (2) to component (1) is about 8:1 or less. Most preferably, the ratio of component (2) to component (1) is in the range of about 2:1 to about 5:1.

The gels will generally include one or more inorganic salts or salts of organic amines or amino acids in an amount effective to provide a gel with the desired original viscosity. Sodium acetate is a particularly preferred salt for this purpose. It is not possible to precisely define the amount of salt to be incorporated into the gel as the amount will vary depending on the type of salt and the carbomer concentration; those skilled in the art will be capable of determining the appropriate quantity. By way of example, however, sodium acetate concentrations in the range of about 0.01 to 0.5% by weight of the gel have generally been found to be appropriate for providing gels of a suitable original and residual viscosity.

The data in Table 1 show the relationship of stability and viscosity to the mixing ratio of gel components.

TABLE 1

STABILITY OF GELS AS A FUNCTION OF THE CARBOMER/PVA RATIO

| Formulation | Viscosity (20° C., 1.5 rpm; Sp 63) | | |
|---|---|---|---|
| | Before Autoclaving | After Autoclaving | % Change |
| 0.25% Carbomer 0.5% PVA 0.07% Na-acetat | 16,700 | 15,500 | −7.2 |
| 0.25% Carbomer 0.5% PVA 0.04% Na-acetat | 38,400 | 32,600 | −15 |
| 0.25% Carbomer 0.6% PVA 0.065% Na-acetat | 22,100 | 21,400 | −5.7 |
| 0.25% Carbomer 0.7% PVA 0.060% Na-acetat | 25,400 | 22,400 | −12 |
| 0.25% Carbomer 0.8% PVA 0.055% Na-acetat | 27,200 | 23,000 | −15 |
| 0.25% Carbomer 1% PVA 0.035% Na-acetat | 24,700 | 20,900 | −15.4 |
| 0.25% Carbomer 2% PVA 0.064% Na-acetat | 20,600 | 11,800 | −42.7 |
| 0.5% Carbomer 0.5% PVA 0.27% Na-acetat | 36,300 | 38,400 | +5.8 |
| 0.5% Carbomer 1% PVA 0.28% Na-acetat | 29,400 | 2,700 | −8.1 |
| 0.5% Carbomer 4% PVA 0.2% Na-acetat | 38,000 | 21,500 | −43.4 |
| 1% Carbomer 1% PVA | 30,200 | 28,100 | −6.9 |

TABLE 1-continued

STABILITY OF GELS AS A FUNCTION OF THE CARBOMER/PVA RATIO

| Formulation | Viscosity (20° C., 1.5 rpm; Sp 63) | | % Change |
|---|---|---|---|
| | Before Autoclaving | After Autoclaving | |
| 1.9% Na-acetat | | | |

TABLE 2

RELATIONSHIP BETWEEN ORIGINAL VISCOSITY AND RESIDUAL VISCOSITY AS A FUNCTION OF THE FORMULATION

| Formulation | Viscosity | Residual Viscosity |
|---|---|---|
| 0.25% Carbomer, 1% PVA 0.01% Na-acetat 0.008% BAC | 59,000 (1.5 rpm) | 25.4 (30 rpm) 29.6 (12 rpm) 58.1 (1.5 rpm) low |
| 0.25% Carbomer, 1% PVA 0.035% Na-acetat 0.008% BAC | 21,000 (1.5 rpm) | 24.0 (30 rpm) 28.6 (12 rpm) |
| 0.25% Carbomer, 1% PVA 0.035% Na-acetat 0.008% BAC | 20,900 (1.5 rpm) | 20.7 (30 rpm) 23.5 (12 rpm) |
| 0.25% Carbomer, 1% PVA 0.07% Na-acetat 0.008% BAC | 7,150 (1.5 rpm) | 20.5 (30 rpm) 22.9 (12 rpm) |
| 0.25% Carbomer, 0.5% PVA 0.07% Na-acetat 0.006% BAC | 13,400 (1.5 rpm) | 20 (30 rpm) |
| 0.25% Carbomer, 0.5% PVA 0.07% Na-acetat | 14,600 (1.5 rpm) | 18.6 (30 rpm) |
| 0.3% Carbomer, 1% PVA 0.1 Na-acetat 0.008% BAC | 19,000 (1.5 rpm) | 38.1 (30 rpm) 46.3 (12 rpm) |
| 0.3% Carbomer, 1% PVA 0.08% Na-acetat | 23,000 (1.5 rpm) | 39.1 (30 rpm) 47.3 (12 rpm) |
| 0.5% Carbomer, 1% PVA 0.26% Na-acetat 0.008% BAC | 22,500 (1.5 rpm) | 518 (1.5 rpm) |
| 0.5% Carbomer, 1% PVA 0.32% Na-acetat 0.008% BAC | 15,000 (1.5 rpm) | 605 (1.5 rpm) 237 (12 rpm) |
| 0.5% Carbomer, 1% PVA 0.26% Na-acetat | 29,600 (1.5 rpm) | 856 (1.5 rpm) |
| 0.5% Carbomer, 1% PVA 0.2% Na-acetat 0.008% BAC 0.136% Timololmaleat | 21,000 (1.5 rpm) | 605 (1.5 rpm) |
| 0.5% Carbomer, 1% PVA 0.2% Na-acetat 0.008% BAC 0.136% Timolomaleat | 20,400 (1.5 rpm) | 513 (1.5 rpm) |
| 1% Carbomer, 1% PVA 1.8% Na-acetat | 30,200 (1.5 rpm) | 19,500 (1.5 rpm) Sp 3 |

KEY:
(a) formulation (components for isotonization and pH adjustment are not listed here);
(b) viscosity, mPa · s, Sp 3, 20° C.;
(c) residual viscosity, mPa · s (addition of a lachrymal film-equivalent amount of salts to the gel), Sp 18, 20° C.

Residual viscosities, as reported in Table 2, may be measured in either of two ways, as described below, (depending upon the magnitude of the viscosity).

Method A—Determination of Residual Viscosity (up to 5,000 mPas)

Instrument: Brookfield Digital Viscometer LVDV-2
Spindle: No. 18
Measuring cup: Small Sample Adapter SC 4
Temperature: 20° C.
Sample: 330 μl of a 20% aqueous solution of sodium chloride (G/V) are added to 25 g of gel (25 ml wide-necked Erlenmeyer flask) and stirred for approximately 5 minutes with a magnetic stirrer.

Measuring: 8 g of the sample prepared for determining the residual viscosity are weighed in the Small Sample Adapter SC and held at a temperature of 20° C. for 30 minutes. Then the viscosity measurement is performed at each of the number of revolutions (rpm) indicated in Table 2. The value is read by the instrument after 15 minutes.

Method B—Determination of Residual Viscosity (viscosities above 5,000 mPas)

Instrument: Brookfield Digital Viscometer LVDV-2
Spindle: No. 3
Measuring cup: 25 ml wide-necked Erlenmeyer flask ($\phi$ of the neck: 3 cm; height of the flask: approx. 6.5 cm)
Sample: 1320 μl of a 20% aqueous solution of sodium chloride (G/V) are added to approximately 100 g gel (100 ml Erlenmeyer flask) and stirred for approximately 5 minutes with a magnetic stirrer.

Measuring: 50 g of the sample prepared for determining the residual viscosity are weighed in bubble-free state in the measuring cup (25 ml Erlenmeyer flask) and held at 20° C. for 30 minutes. Then the viscosity measurement is performed at each of the number of revolutions (rpm) indicated in Table 2. The value is read by the instrument after fifteen minutes.

The gels of this invention preferably exhibit a residual viscosity in the range of about 20 to 2,000 mPas. Residual viscosity of a gel may be measured, using a Brookfield viscometer, upon addition of 300 μl of a 20% NaCl solution to each 25 g gel sample.

Several conclusions can be drawn from the data in Table 2. First, the resulting residual viscosity depends almost exclusively on the amount of carbomer used. It is almost completely independent of the original viscosity and of the amount of PVA. Second, the residual viscosity increases drastically with the amount of carbomer; at a carbomer content of 1%, the viscosity is already in a range which is no longer acceptable in terms of compatibility with the eye. Third, the original viscosity depends on the concentration of salt and on the concentration of carbomer; that is, for the same carbomer content, the original viscosity decreases as the salt concentration increases. As the carbomer concentration increases, more salt must be added to arrive at the same original viscosity.

Because it is necessary to add a base, usually NaOH, to form a polyacrylate gel, the gels claimed in accordance with the invention generally also contain bases. Especially good results are obtained in our case with the amino acid lysine as the base. In addition to lysine, other basic amino acids such as ornithine, a,m-diaminobutyric acid, arginine, histidine, and even hydroxylysine (a component of natural collagen) are also suitable. In principle, a gel can be formed with any base. For standard commercial eye gels, NaOH is used. Lysine has been selected in accordance with the invention, because, after the gel has been applied to the skin, it feels "smoother" and is highly compatible. Gels can also be formed by the use of amines.

Because gels for use on the eye are usually supposed to be isotonic, these gels may be isotonized by the use of suitable nonionic agents. As a rule, sorbitol or mannitol is used for this purpose. Glycerol can also be used. The eye tolerates osmolarities in the range of 100–450 mOsmol/L. As a rule, eye drops are adjusted with an isotonizing agent, namely, with a salt, to about 280–320 mOsmol/L. Salts (ions) cannot be used for carbomers in the claimed concentrations for the reasons discussed above, because they would destroy the structure of the gel.

Gels of this invention without a pharmacologically active component can be used as a substitute for lachrymal fluid. The gels of this invention are also suitable as vehicles for active ingredients e.g., any active ingredient normally used in ophthalmology. Such active ingredients, and the therapeutically effective amounts thereof, would be known to those skilled in the art. It is very difficult to incorporate organic bases active ingredients and preservatives of the "quat" (quaternary ammonium compound) type into clear and stable polyacrylate gels. According to the invention, formulations and processes are discovered which make this possible.

Gels of this invention may contain a preservative. Those skilled in the art would know which preservatives are ophthalmologically compatible and the quantities to use. An example of a conventional preservative is benzalkonium chloride (BAC); in this regard, it must be remembered that the addition of a preservative is prescribed for ophthalmologic agents packaged in multidose containers. The compatibility between carbomers and benzalkonium chloride is poor. The addition of a second, highly water-soluble polymer prevents the interfering effects (such an addition also makes it possible to incorporate active ingredients in dissolved form). Other preservatives are also compatible with the combination according to the invention, e.g., the preservatives thiomersal, chlorhexidine gluconate/acetate, and Parabens, all of which are well tolerated by the eye. BAC can be considered representative of the group of the "quats" and also for polymers and quat-like substances.

The gels according to the invention are produced as follows: In a reactor which can be both heated and evacuated and which is equipped with a stirrer and homogenizer, an aqueous solution of the polymer(s) to be combined with the carbomer is produced at elevated temperature. The isotonizing agent, the active ingredient(s), and any preservatives and/or other conventional additives desired are dissolved in this solution. In the next step, the carbomer is dispersed in the solution, and the gel is formed by the addition of a base. Finally, the gel is briefly homogenized and deaerated (homogenization and deaeration can be carried out during the cooling phase).

The following examples explain the invention but are not intended to limit it in any way. All percentages are by weight.

FORMULATION EXAMPLES

All of the following formulations are hydrogels (water-based).

| Example 1 Composition in %: | |
| --- | --- |
| polyvinyl alcohol | 1 |
| sorbitol | 4.5 |
| carbomer (polyacrylic acid) | 0.19 |
| DL-lysine | 0.34 |
| benzalkonium chloride | 0.008 |

Production 13.5 g of sorbitol was dissolved in 80 g of water in an evacuatable reactor equipped with a stirrer and a homogenizer. 75 g of a 4% polyvinyl alcohol solution was added, and the resulting solution was heated to 70°-80° C. After the homogenizer was turned on, 0.57 g of carbomer was added in small portions to the solution; after all the portions had been added, the homogenizer was allowed to run for an additional 5 minutes to complete the dispersion process. 100 g of a 0.02% solution of benzalkonium chloride was dripped slowly into this mixture with stirring. The gel was formed by the addition of 31 g of a 3.4% solution of lysine. During the cooling phase, the reactor was evacuated to deaerate the gel.

Viscosity (Brookfield viscometer): 38.700 mPa.s after autoclaving (spindle 3, 1.5 rpm, 20° C.), pH 7.7.

| Example 2 Composition in %: | |
| --- | --- |
| polyvinyl alcohol | 1 |
| sorbitol | 4.5 |
| sodium acetate, anhydrous | 0.04 |
| carbomer (polyacrylic acid) | 0.25 |
| DL-lysine | 0.43 |
| benzalkonium chloride | 0.008 |

Production 13.5 g of sorbitol was dissolved in 0.12 g of water in an evacuatable reactor equipped with stirrer and homogenizer; 75 g of a 4% polyvinyl alcohol solution was added, and the resulting solution was heated to 70-80° C.". After the homogenizer had been turned on, 0.57 g of carbomer was added to the solution in small portions; after all the portions had been added, the homogenizer was allowed to run for an additional 5 minutes to complete the dispersion process. The gel was formed by the addition of 16.3 g of a 7.9% solution of lysine. 14.5 mL of a 0.17% solution of benzalkonium chloride was dripped slowly with stirring into the gel. During the cooling phase, the reactor was evacuated to deaerate the gel.

Viscosity (Brookfield viscometer): 16,900 mPa.s after autoclaving (spindle 3, 1.5 rpm, 20° C.), pH 7.6.

| Example 3 Composition in %: | |
| --- | --- |
| polyvinyl alcohol | 1 |
| sorbitol | 4.5 |
| sodium acetate, anhydrous | 0.14 |
| carbomer (polyacrylic acid) | 0.5 |
| DL-lysine | 0.89 |
| benzalkonium chloride | 0.008 |

Production as in Example 2.

Viscosity (Brookfield viscometer): 36,800 mPa.s after autoclaving (spindle 3, 15 rpm, 20° C.) pH 7 2

| Example 4 Composition in %: | |
| --- | --- |
| Dextran 70 | 2.0 |
| sorbitol | 4.8 |
| carbomer (polyacrylic acid) | 0.16 |
| DL-lysine | 0.27 |
| benzalkonium chloride | 0.008 |

Production 19.2 g of sorbitol and 8 g of dextran were dissolved in 221 g of water at 40°-60° C. in an evacuatable reactor equipped with stirrer and homogenizer. After the homogenizer had been turned on, 0.64 g of carbomer was added to the solution in small portions; after all the portions had been added, the homogenizer was allowed to run for an additional 5 minutes to complete the dispersion process. 100 g of a 0,032% solution of benzalkonium chloride was dripped slowly with stirring into this mixture. The gel was formed by the addition of 51 g of a 2.1% solution of lysine. During the cooling phase, the reactor was evacuated to deaerate the gel.

Viscosity (Brookfield viscometer): 30,200 mPa.s after autoclaving (spindle 3, I.S rpm, 20° C.), pH 7.4.

| Example 5 Composition in %: | |
|---|---|
| polyvinyl alcohol | 1 |
| sorbitol | 4.5 |
| timolol hydrogen maleate | 0.5 |
| carbomer (polyacrylic acid) | 0.5 |
| DL-lysine | 1.1 |
| benzalkonium chloride | 0.008 |

Production 13.5 g of sorbitol was dissolved in 80 g of water in an evacuatable reactor equipped with stirrer and homogenizer. 75 g of a 4% polyvinyl alcohol solution was added, and the resulting solution was heated to 70°–80° C. 1.5 g of timolol hydrogen maleate was dissolved in the mixture, and after the homogenizer had been turned on, 1.5 g of carbomer was added to the solution in small portions. After all the portions had been added, the homogenizer was allowed to run for an additional 5 minutes to complete the dispersion process. 100 g of a 0.024% solution of benzalkonium chloride was dripped slowly with stirring into this mixture. The gel was formed by the addition of 28.3 g of a 11.7% solution of lysine. During the cooling phase, the reactor was evacuated to deaerate the gel.

Viscosity (Brookfield viscometer): 33,200 mPa.s after autoclaving (spindle 3, 1.5 rpm, 20° C.), pH 7.4.

| Example 6 Composition in %: | |
|---|---|
| polyvinyl alcohol | 1 |
| mannitol | 5 |
| carbomer (polyacrylic acid) | 0.165 |
| DL-lysine | 0.2 |
| benzalkonium chloride | 0.008 |
| prednisolone acetate | 0.5 |

Production 15 g of mannitol was dissolved in 170 g of water in an evacuatable reactor with stirrer and homogenizer. 75 g of a 4% polyvinyl alcohol solution was added, and the resulting solution was heated to 70°–80° C.

After the homogenizer had been turned on, 0,495 g of carbomer was added to the solution in small portions; after all the portions had been added, the homogenizer was allowed to run for another 5 minutes to complete the dispersion process. The gel was formed by the addition of 15.75 g of a 4.76% solution of lysine. During the cooling phase, the reactor was evacuated to deaerate the gel.

A homogenizer was used to distribute finely 1.5 g of prednisolone acetate in 23 g of water, which contained 0.15 mL of a 16.4% benzalkonium chloride solution. The resulting suspension was added in small portions to the gel. After the addition was completed, the stirrer was allowed to run for one more hour to complete the homogenization process.

Viscosity (Brookfield viscometer): 35,700 mPa.s after autoclaving (spindle 3, 1.5 rpm, 20° C.), pH 7.0.

What is claimed is:

1. An ophthalmologic gel having a viscosity in the range of about 10,000 to about 50,000 mPa.s comprising (1) about 0.05 to about 3% by weight of one or more polyacrylates and (2) about 0.1 to about 10% by weight one or more watersoluble, physiologically compatible polymers selected from the group consisting of polyvinyl alcohol, dextran, and mixtures thereof.

2. A gel of claim 1 wherein the amount of component (1) is equal to or less than that of component (2).

3. A gel of claim 1.wherein the ratio of component (2) to component (1) is about 8:1 or less.

4. A gel of claim 3 wherein the ratio of component (2) to component (1) is in the range of about 2:1 to about 5:1.

5. A gel of claim 1 which exhibits a residual viscosity in the range of about 20 to 2,000 mPas.

6. A gel of claim 1 in which said physiologically compatible polymer is polyvinyl alcohol.

7. A gel of claim 1 in which said polyvinyl alcohol has a molecular weight in the range of about 15,000 to about 200,00 and a degree of hydrolysis of at least about 99%.

8. A gel of claim 3 in which said physiologically compatible polymer is polyvinyl alcohol.

9. A gel of claim 4 in which said physiologically compatible polymer is polyvinyl alcohol.

10. A gel of claim 3 which exhibits a residual viscosity in the range of about 20 to 2,000 mPas.

11. A gel of claim 4 which exhibits a residual viscosity in the range of about 20 to 2,000 mPas.

12. A gel of claim 6 which exhibits a residual viscosity in the range of about 20 to 2,000 mPas.

13. A gel of claim 8 which exhibits a residual viscosity in the range of about 20 to 2,000 mPas.

14. A gel of claim 9 which exhibits a residual viscosity in the range of about 20 to 2,000 mPas.

15. A gel of claim 1 which further comprises about 0.01 to about 0.5% sodium acetate.

16. A gel of claim 1 wherein said polyacrylate has a molecular weight in the range of about 1,000,000 to about 4,000,000.

17. A gel of claim 14 wherein said polyacrylate has a molecular weight in the range of about 1,000,000 to about 4,000,000.

18. A gel of claim 1 which further comprises lysine.

19. A gel of claim 1 which further comprises one or more isotonizing agents selected from the group consisting of mannitol and sorbitol.

20. A gel of claim 1 which further comprises an effective preservative amount of benzalkonium chloride.

21. A gel of claim 1 which further comprises a therapeutically effective amount of a pharmacologically active component.

22. A gel of claim 1 in which the ratio of component (2) to component (1) is in the range of about 1:1 to about 5:1.

23. A gel of claim 1 in which the polyacrylate content is less than about 1% by weight.

\* \* \* \* \*